United States Patent

Torii et al.

Patent Number: 5,986,091
Date of Patent: Nov. 16, 1999

[54] PROCESS FOR PREPARATION OF β-LACTAM COMPOUNDS

[75] Inventors: Sigeru Torii; Hideo Tanaka, both of Okayama-ken; Michio Sasaoka; Yutaka Kameyama, both of Tokushima, all of Japan

[73] Assignee: Otsuka Kagaku Kabushiki Kaisha, Osaka, Japan

[21] Appl. No.: 08/952,526

[22] PCT Filed: Mar. 7, 1996

[86] PCT No.: PCT/JP97/00709
§ 371 Date: Nov. 12, 1997
§ 102(e) Date: Nov. 12, 1997

[87] PCT Pub. No.: WO97/33891
PCT Pub. Date: Sep. 18, 1997

[30] Foreign Application Priority Data

Mar. 13, 1996 [JP] Japan ................ 8-085833

[51] Int. Cl.[6] ............ C07D 501/59; C07D 205/095
[52] U.S. Cl. .............................. 540/215; 540/358
[58] Field of Search ............................ 540/358, 215

[56] References Cited

U.S. PATENT DOCUMENTS 5,204,458  4/1993  Torri et al. .................... 540/222

FOREIGN PATENT DOCUMENTS

| 4-282387 | 7/1992 | Japan . |
| 4-211055 | 8/1992 | Japan . |
| 4-283584 | 10/1992 | Japan . |
| 7-61967 | 3/1996 | Japan . |
| 8-245573 | 9/1996 | Japan . |

OTHER PUBLICATIONS

Patent Abstracts of Japan, Publication No. 08245573 A, Publication Date: Sep. 24, 1996.
Patent Abstracts of Japan, Publication No. 07061967 A, Publication Date: Mar. 7, 1995.
Patent Abstracts of Japan, Publication No. 04211055 A, Publication Date: Aug. 3, 1992.
Patent Abstracts of Japan, Publication No. 04283584 A, Publication Date: Oct. 8, 1992.
Derwent Abstract for Japan 4–282387, Jul. 10, 1992.

Primary Examiner—Mark L Berch
Attorney, Agent, or Firm—Kubovcik & Kubovcik

[57] ABSTRACT

The present invention provides a process for preparing an allenyl β-lactam compound represented by the formula (II) or a process for preparing a 3-halocephem compound of the formula (III) by altering the reaction conditions with use of a β-lactam halide compound represented by the formula (I) serving as the starting material

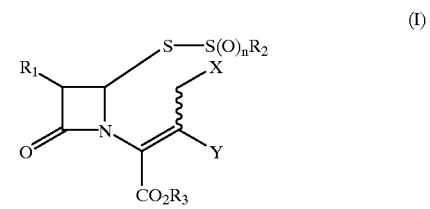

(I)

wherein $R_1$ is a hydrogen atom, amino or protected amino, $R_2$ is aryl which may have a substituent, n is 0 to 2, $R_3$ is a hydrogen atom or carboxylic acid protective group, X is a halogen atom, and Y is a halogen atom or a leaving group

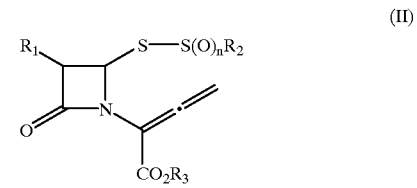

(II)

wherein $R_1$, $R_2$, n and $R_3$ are as defined above

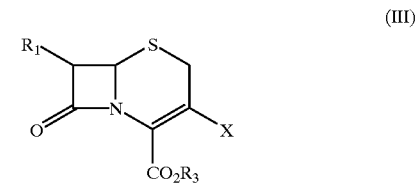

(III)

wherein $R_1$, $R_3$ and X are as defined above.

6 Claims, No Drawings

PROCESS FOR PREPARATION OF β-LACTAM COMPOUNDS

TECHNICAL FIELD

The allenyl β-lactam compounds and 3-halocephem compounds of the present invention are important intermediates, from which readily derivable are 3-chlorocephalosporin intermediates, i.e., useful starting materials for cefaclor which has antibacterial activity on a wide variety of gram-positive or gram-negative bacteria and which is widely used as an oral drug. These compounds are in prevalent use industrially.

BACKGROUND ART

The allenyl β-lactam compound of the invention represented by the formula (II) is conventionally prepared, for example, by reacting a tertiary organic base with the starting material in an organic solvent according to the process disclosed in JP-A-282359/1992. However, this compound as contained in the resulting reaction mixture is unstable owing to the presence of an excess of the tertiary organic base or a salt of the base and sulfonic acid, so that the reaction mixture usually requires repetition of a cumbersome procedure involving extraction and concentration after the completion of the reaction. This procedure takes time in the case of quantity production, consequently entailing problems such as a marked reduction in the yield of the isolated product. Thus, a satisfactory feasible process has yet to be developed for preparing the allenyl β-lactam compound.

Reports have been made on widely acceptable processes for preparing 3-halogenated cephem derivatives represented by the formula (III). These processes include a process which uses a 3-hydroxycephem compound represented by the formula (IV) and serving as the starting material and involves conversion of the hydroxyl group to trifluoromesyloxy group and the subsequent reaction with a lithium halide as disclosed in J. Org. Chem., 54, 4962(1989), a process wherein a reactive chlorine or bromine compound (such as phosphorus trichloride, phosphorus oxychloride or thionyl bromide) is reacted with a 3-hydroxycephem compound in dimethylformamide as disclosed in JP-A- 116095/1974, and further a process wherein an alkali metal salt or alkaline earth metal salt of a halogen is reacted with an allenyl β-lactam compound as disclosed in JP-A-282387/1992

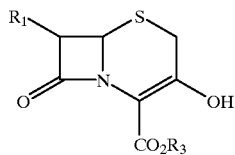

(IV)

wherein $R_1$ and $R_3$ are as defined below.

The first of the processes requires the use of the 3-hydroxycephem compound as the starting material which compound itself is difficult to prepared and is therefore in no way practically feasible. The second process inevitably forms 3-sulfonylcephem or 3-thiocephem as a by-product due to the recombination of sulfinate ion or thiolate ion which is released on ring closure, consequently giving the desired 3-halogenated cephem derivative in a yield of as low as up to 70%.

An object of the present invention is to overcome the drawbacks of the foregoing conventional processes and to provide a process capable of readily preparing the desired allenyl β-lactam compound and 3-halogenated cephem compound from the same starting material in a high yield with a high purity merely by using different reaction conditions for the different compounds.

DISCLOSURE OF THE INVENTION

The present invention provides a process for preparing an allenyl β-lactam compound represented by the formula (II) which process is characterized in that a β-lactam halide compound represented by the formula (I) is reduced with a zero-valent metal

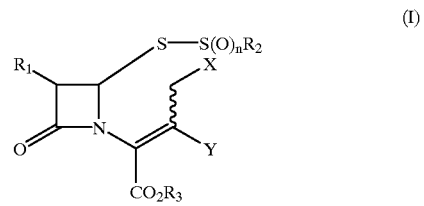

(I)

wherein $R_1$ is a hydrogen atom, amino or protected amino, $R_2$ is aryl which may have a substituent, n is 0 to 2, $R_3$ is a hydrogen atom or carboxylic acid protective group, X is a halogen atom, and Y is a halogen atom or a leaving group

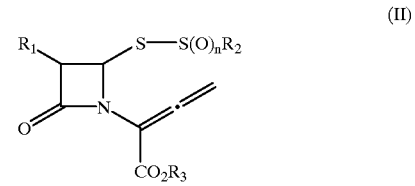

(II)

wherein $R_1$, $R_2$, n and $R_3$ are as defined above.

In solving the problems of the foregoing known processes while developing processes for preparing allenyl β-lactam compounds, we found that the decomposition of the allenyl β-lactam compound is attributable to the presence of a very small excess of the tertiary organic base or a salt of the tertiary organic base and sulfonic acid remaining after the completion of the allenylation reaction. This finding has led us to the discovery of the entirely novel fact that when the compound of the formula (I) is subjected to a reducing elimination reaction which is entirely different from the conventional 1,2-elimination reaction using a base, an allenyl β-lactam compound represented by the formula (II) can be isolated from the reaction mixture by a usual procedure in a high yield and with a high purity without using the tertiary organic base which causes decomposition of the allenyl β-lactam compound. Thus, the invention has been accomplished.

The present invention further provides a process for preparing a 3-halocephem compound represented by the formula (III) which process is characterized by reducing a β-lactam halide compound represented by the formula (I) with a zero-valent metal and effecting a ring closure reaction at the same time by nucleophilic attack of the resulting halogen ion to obtain the 3-halocephem compound

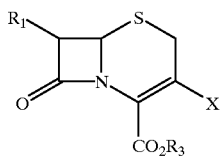

(III)

wherein $R_1$, $R_3$ and X are as defined above.

More specifically, we have found the entirely novel fact that the same starting material as above, i.e., the compound of the formula (I), undergoes a reducing 1,2-elimination reaction and a ring closure reaction at the same time, giving a 3-halocephem compound of the formula (III) straightforwardly with a high purity and in a high yield, merely when altered reaction conditions are used. (When the material is reacted at room temperature using, for example, aluminum as a reducing agent, the reaction selectively gives only the allenyl β-lactam compound if the reaction time is short, or selectively affords the 3-halocephem compound which is a cyclization product if the reaction time is long, although the result will vary with the reducing agent, Lewis acid, reaction temperature, reaction time, etc.). Thus, the present invention has been accomplished.

Examples of groups mentioned herein are as follows.

Exemplary of the protected amino represented by $R_1$ are amido groups such as phenoxyacetamido, p-methylphenoxyacetamido, p-methoxyphenoxyacetamido, p-chlorophenoxyacetamido, p-bromophenoxyacetamido, phenylacetamido, p-methylphenylacetamido, p-methoxyphenylacetamido, p-chlorophenylacetamido, p-bromophenylacetamido, phenylmonochloroacetamido, phenyldichloroacetamido, phenylhydroxyacetamido, thienylacetamido, phenylacetoxyacetamido, α-oxophenylacetamido, benzamido, p-methylbenzamido, p-methoxybenzamido, p-chlorobenzamido, p-bromobenzamido, phenylglycylamido, phenylglycylamido having protected amino, p-hydroxyphenylglycylamido, p-hydroxyphenylglycylamido having protected amino and/or protected hydroxyl, etc.; imido groups such as phthalimido, nitrophthalimido, etc., in addition to the groups disclosed in Theodora W. Greene, 1981, "Protective Groups in Organic Synthesis" (hereinafter referred to merely as the "literature"), Chap. 7 (pp. 218~287). Examples of protective groups for the amino of phenylglycylamido group and p-hydroxyphenylglycylamido group are those disclosed in the literature, Chap. 7 (pp. 218~287). Examples of protective groups for the hydroxyl of p-hydroxyphenylglycylamido group are those disclosed in the literature, Chap.2 (pp. 10~72).

Examples of aryl and substituted aryl represented by $R_2$ are phenyl, naphthyl, nitrogen-containing heterocyclic group, etc. Exemplary of the nitrogen-containing heterocyclic groups are benzothiazol group, triazol group, thiazol group, tetrazol group, etc. Exemplary of the substituent which may be substituted in the aryl are halogen atoms (such as fluorine atom, chlorine atom, bromine atom, iodine atom), straight-chain or branched $C_{1-4}$ alkoxyl groups (such as methoxy, ethoxy), straight-chain or branched $C_{1-4}$ alkylthio groups (such as methylthio, ethylthio), straight-chain or branched $C_{1-4}$ alkylsulfonyloxy groups (such as methanesulfonyloxy, trifluoromethanesulfonyloxy), aromatic sulfonyloxy or substituted aromatic sulfonyloxy (such as benzenesulfonyloxy, toluenesulfonyloxy), straight-chain or branched $C_{1-4}$ alkyl groups (such as methyl, ethyl), amino, amino which has as a substituent one or two straight-chain or branched $C_{1-4}$ alkyl groups (such as methylamino, dimethylamino, ethylamino, diethylamino), hydroxyl, acyloxy group represented by R'COO—wherein R' is phenyl, tolyl, or straight-chain or branched $C_{1-4}$ alkyl group (such as phenylcarbonyloxy, acetyloxy), acyl group represented by R'CO—wherein R' is as defined above (such as phenylcarbonyl, acetyl), nitro, cyano, phenyl, etc. When the aryl represented by $R_2$ is phenyl group, the aryl may have 1 to 5, especially 1, 2 or 3, same or different groups selected from among the above substituents. When the aryl represented by $R_2$ is naphthyl group, the aryl may have 1 to 7, especially 1, 2 or 3, same or different groups selected from among the above substituents. Exemplary of the carboxylic acid protecting group represented by $R_3$ are allyl, benzyl, p-methoxybenzyl, p-nitrobenzyl, diphenylmethyl, trichloromethyl, tert-butyl, and those disclosed in the literature, Chap. 5 (pp. 152~192). Examples of halogen atoms represented by X, Y are fluorine, chlorine, bromine or iodine atom. Exemplary of the leaving groups represented by Y are a halogen atom lower alkylsulfonyloxy or substituted lower alkylsulfonyloxy (such as methanesulfonyloxy, trifluoromethanesulfonyloxy, trichloromethanesulfonyloxy), aromatic sulfonyloxy or substituted aromatic sulfonyloxy (such as benzenesulfonyloxy, toluenesulfonyloxy), halogenated sulfonyloxy or substituted halogenated sulfonyloxy (such as fluoromethanesulfonyloxy), lower alkylphosphonyloxy or substituted lower alkylphosphonyloxy (such as trimethylphosphonyloxy, triethylphonyloxy, tributylphosphonyloxy), aromatic phosphonyloxy or substituted aromatic phosphonyloxy (such as triphenylphosphonyloxy, tritolylphosphonyloxy), etc.

The β-lactam compound represented by the formula (I) for use as a starting material of the present invention can be prepared by a method, for example, as shown below. Namely, a halogenating agent or agent for generating a leaving group is caused to act on the hydroxyl group of the β-lactam halide compound of the formula (V), whereby the compound (V) can be converted to a β-lactam halide compound represented by the formula (I). Alternatively, the compound (V) is acted on with the leaving group generating agent first and then with the halogenating agent, whereby the β-lactam halide compound (I) can be prepared under milder conditions

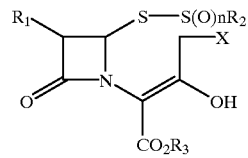

(V)

wherein $R_1$, $R_2$, $R_3$ and X are as defined above, n is 0 to 2.

Examples of useful halogenating agents are phosphorus (V) chlorides such as phosphorus oxychloride and pentachloride, phosphorus(III) chlorides and bromides such as phosphorus trichloride and phosphorus tribromide, triarylphosphine-halogen complexes such as triarylphosphine-dichlorine complex and triarylphosphine-dibromine complex which may have a substituent, mixtures of a triarylphosphine or trialkylphosphine which may have a substituent and a halogen molecule, thionyl halides such as thionyl chloride and thionyl bromide, sulfonyl halides such as sulfonyl chloride and sulfonyl bromide, etc. Usual halogenating agents for the hydroxyl group are usable without any particular limitations. These halogenating agents are used usually in an amount of about 1 to about 50 moles, preferably about 1 to about 10 moles, per mole of the compound of the formula (I). The halogenating agent can be used in combination with an inorganic base such as sodium bicarbonate or sodium carbonate, organic base such as triethylamine, ethyldiisopropylamine or N,N-dimethylaniline, or basic resin such as Amberlite XE-583. While the above halogenating agents are usable as the halogenating agent to be used subsequently to the leaving group generating agent used first, other examples of such agents usable for the subsequent reaction include alkali metal halide salts such as lithium chloride and lithium bromide, alkaline-earth metal halide salts such as calcium chloride and calcium bromide, and aluminum halide salts such as aluminum chloride and aluminum bromide. These halogen salts are used usually in an amount of about 1 to about 50 moles, preferably about 1 to about 10 moles, per mole of the compound of the formula (IV). The halogen salts are usable singly or in combination of at least two of them.

Examples of leaving group generating agents usable are methanesulfonyl chloride, trifluoromethanesulfonyl chloride and like lower alkylsulfonyl chlorides which may have a substituent, benzenesulfonyl chloride, toluenesulfonyl chloride and like aromatic sulfonic acid chlorides which may have a substituent, methanesulfonic anhydride, trifluoromethanesulfonic anhydride and like lower alkylsulfonic anhydrides which may have a substituent, benzenesulfonic anhydride, toluenesulfonic anhydride and like aromatic sulfonic anhydrides which may have a substituent, diethylphosphonyl chloride and like lower alkylphosphoryl chlorides which may have a substituent, diphenylphosphonyl chloride and like aromatic phosphoryl chlorides which may have a substituent, etc. These agents are used usually in an amount of about 1 to about 50 moles, preferably about 1 to about 10 moles, per mole of the compound of the formula (V). The leaving group generating agent can be used in combination with, for example, an inorganic base such as sodium bicarbonate or sodium carbonate, organic base such as triethylamine, ethyldiisopropylamine or N,N-dimethylaniline, or basic resin such as Amberlite XE-583. Examples of substituents which may be present in these lower alkylsulfonyl chlorides, lower alkylsulfonyl anhydrides and lower alkyl phosphoryl chlorides are halogen atoms (such as fluorine, chlorine, bromine and iodine atoms), straight-chain or branched $C_{1-4}$ alkoxyl groups (such as methoxy, ethoxy), straight-chain or branched $C_{1-4}$ alkylthio groups (such as methylthio, ethylthio), straight-chain or branched $C_{1-4}$ alkylsulfonyloxy groups (such as methanesulfonyloxy, trifluoromethanesulfonyloxy), straight-chain or branched $C_{1-4}$ alkyl groups (such as methyl, ethyl), amino, amino which has as a substituent one or two straight-chain or branched $C_{1-4}$ alkyl groups (such as methylamino, dimethylamino, ethylamino, diethylamino), acyloxy group represented by R'COO—wherein R' is phenyl, tolyl, or straight-chain or branched $C_{1-4}$ alkyl group (such as phenylcarbonyloxy, acetyloxy), acyl group represented by R'CO— wherein R' is as defined above (such as phenylcarbonyl, acetyl), nitro, cyano, phenyl, etc. The lower alkylsulfonyl chlorides or anhydrides or lower alkylphosphoryl chlorides may have 1 to 5, preferably 1, 2 or 3, such substituents which are different or of the same kind. Examples of substituents which may be present in the aromatic sulfonyl chlorides, aromatic sulfonyl anhydrides and aromatic phosphoryl chlorides are the same as those exemplified for the lower alkylksulfonyl chlorides or anhydrides or lower alkylphosphoryl chlorides. In the case where the aromatic group is phenyl, 1 to 5, preferably 1, 2 or 3, such substituents may be present, or when the aromatic group is naphthyl, 1 to 7, preferably 1, 2 or 3, such substituents may be present. These substituents are different or of the same kind.

The reaction is conducted in a suitable solvent. Examples of solvents useful in the reaction are lower alkyl esters of lower carboxylic acids such as methyl formate, ethyl formate, propyl formate, butyl formate, methyl acetate, ethyl acetate, propyl acetate, butyl acetate, methyl propionate and ethyl propionate, ketones such as acetone, methyl ethyl ketone, methyl propyl ketone, methyl butyl ketone, methyl isobutyl ketone and diethyl ketone, ethers such as diethyl ether, ethyl propyl ether, ethyl butyl ether, dipropyl ether, diisopropyl ether, dibutyl ether, methyl cellosolve and dimethoxyethane, cyclic ethers such as tetrahydrofuran, dioxane and dioxolan, nitriles such as acetonitrile, propionitrile, butyronitrile, isobutyronitrile and valeronitrile, substituted or unsubstituted aromatic hydrocarbons such as benzene, toluene, xylene, chlorobenzene and anisole, hydrocarbon halides such as dichloromethane, chloroform, dichloroethane, trichloroethane, dibromoethane, propylene dichloride, carbon tetrachloride and Freons, aliphatic hydrocarbons such as pentane, hexane, heptane and octane, cycloalkanes such as cyclopentane, cyclohexane, cycloheptane and cyclooctane, amides such as dimethylformamide, diethylformamide and dimethylacetamide, cyclic amides such as N-methylpyrrolidinone, dimethylsulfoxide, etc. These solvents are used singly or in admixture of at least two of them. These solvents may contain water as required. These solvents are used in an amount of about 10 to about 200 liters, preferably about 20 to about 100 liters, per kilogram of the compound of the formula (V) The reaction is conducted usually at −78° C. to 60° C., preferably—40° C. to 30° C. Examples of useful bases are N,N,N-tri lower alkyl amines such as trimethylamine, dimethylethylamine, triethylamine and diisopropylethylamine, N-lower alkyl azacycloalkanes such as N-methylpiperidine and N-ethylpiperidine, N-lower alkyl azaoxycycloalkanes such as N-methylmorpholine and N-ethylmorpholine, N-phenyl lower alkyl-N,N-di lower alkyl amines such as N-benzyl-N,N-dimethylamine and N-benzyl-N,N-diethylamine, N,N-dialkyl aromatic amines such as N,N-dimethylaniline, nitrogen-containing aromatic amines such as pyridine, bicycloamines such as diazabicycloundecene and diazabicyclononene, and a mixture of these amines. These bases are used usually in an amount of 1 to 10 equivalents based on the β-lactam compound of the formula (V). When required, it is recommended the base is added until the β-lactam compound of the formula (V) is consumed. The resulting halogenated β-lactam compound of the formula (I) can be isolated by the usual purification method but can be used in the next reaction without purification.

The β-lactam halide compound represented by the formula (I) and obtained in this way can be converted into an allenyl β-lactam compound represented by the formula (II) when reduced with a zero-valent metal, or into a 3-halocephem compound represented by the formula (III) merely by altering the conditions for the former reaction. The present reaction is a stepwise reaction, so that the compound (II) only can be obtained by quenching the reaction, for example, upon high performance liquid chromatography (HPLC) detecting disappearance of the material compound (I) and indicating presence of the compound (II) only. If the reaction is allowed to further continue as it is without quenching, the ring closure reaction proceeds to give the compound (III) straightforwardly.

Examples of the zero-valent metals are aluminum, magnesium, zinc, iron, nickel, tin, lead, etc., among which aluminum, magnesium, zinc and tin are desirable to use. The shape of these metals is not limited particularly but can be any of a wide variety of forms such as powder, plate, foil, lump and wire. Preferably, the metal to be used is in the form of a powder or foil. The particle size of the powdery metal is preferably about 50 to about 300 mesh although variable over a wide range. These metals are used usually in an amount of about 1 to about 50 moles, preferably about 1 to about 20 moles, per mole of the compound of the general formula (I)

When the above reaction of the invention is conducted in the presence of a Lewis acid, the zero-valent metal is activated to result in a higher reaction velocity. The presence of the acid is desirable especially in the case where the starting compound is low in reactivity since the reaction then proceeds smoothly to completion without forming an increased amount of by-product.

Examples of Lewis acids are lithium halide salts such as lithium chloride and lithium bromide, calcium halide salts such as calcium chloride and calcium bromide, aluminum halide salts such as aluminum chloride and aluminum bromide, lead compounds (such as lead fluoride, lead chloride, lead bromide, lead iodide and like lead halides, lead nitrate, lead sulfate, lead perchlorate, lead borate, lead carbonate, lead phosphate and like inorganic salts of lead, lead acetate, lead oxalate, lead stearate and like fatty acid salts of lead, lead oxide and lead hydroxide), copper compounds (such as copper fluoride, copper chloride, copper bromide, copper iodide and like copper halides, copper nitrate, copper sulfate, copper perchlorate, copper borate, copper carbonate, copper phosphate and like inorganic salts of copper, and copper oxalate), titanium compounds (such as titanium fluoride, titanium chloride, titanium bromide, titanium iodide and like titanium halides, and titanium nitrate, titanium sulfate and like inorganic salts of titanium), tin compounds [such as tin(IV) chloride, tin(II) chloride and like tin halides), bismuth compounds (such as bismuth fluoride, bismuth chloride, bismuth bromide, bismuth iodide and like bismuth halides, bismuth nitrate, bismuth sulfate and like inorganic salts of bismuth), antimony compounds (such as antimony fluoride, antimony chloride, antimony bromide, antimony iodide and like antimony halides, antimony sulfate and like inorganic salts of antimony, and antimony oxide), and nickel compounds (such as nickel fluoride, nickel chloride, nickel bromide, nickel iodide and like nickel halides, nickel nitrate, nickel sulfate, nickel perchlorate, nickel borate, nickel carbonate, nickel phosphate and like inorganic salts of nickel, nickel acetate and like fatty acid salts of nickel, tetrachloronickel(II) tetraethylammonium, tetrabromonickel(II) tetraethylammonium, hexamminenickel(II), tris(ethylenediamine)nickel(II) sulfate, ethylenediaminetetraaquanickel(II) sulfate monohydrate, dinitrobis(ethylenediamine)nickel(II), bis(N,O-dimethylethylenediamine)nickel(II) perchlorate and like inorganic complexes of nickel, dichloro(bipyridyl)nickel(II), chloro(n-cyclopentadienyl) (triphenylphosphine)nickel(II), dibromobis(triphenylphosphine)nickel(II), dichlorobis{1,1'-bis(diphenylphosphino)ferrocene}nickel(II) and like organic complexes of nickel(II), and tetrakis(triphenylphosphine)-nickel(0), tris(triphenylphosphine) nickel(0), nickel(0)acetylacetonato, nickel(0) hexafluoroacetylacetonato and like organic complexes of nickel(0)). These metal compounds may be used singly or as a mixture of at least two of them. These metal compounds are used usually in an amount of 0.0001 to 30 moles, preferably 0.001 to 10 moles, per mole of the compound of the general formula (I).

Examples of useful solvents for the present reaction are the same as those for use in the preparation of the compound of the formula (I).

The reaction is conducted at a temperature usually of −10 to 80° C., preferably of 0 to 50° C. The reaction of the invention proceeds satisfactorily even around room temperature. Further when required, the reaction can be conducted within a closed container or in an inert gas such as nitrogen gas. The allenyl β-lactam compounds of the formula (II) and 3-halocephem compounds of the formula (III) obtained can be isolated by a usual purification procedure such as extraction and column chromatography.

BEST MODE OF CARRYING OUT THE INVENTION

The present invention will be described in greater detail with reference to the following examples, in which Ph stands for phenyl and Et for ethyl.

EXAMPLE 1

A 100 mg quantity of compound (Ia) ($R_1$=PhCH$_2$CONH, $R_2$=Ph, $R_3$=CH$_2$C$_6$H$_4$OCH$_3$-p, X=Cl, Y=Cl, n=2), 0.5 equivalent of aluminum chloride and 10 equivalents of aluminum foil were measured out into a 10 ml flask of the egg plant type, followed by stirring at room temperature for 2 hours with addition of 2 ml of N-methyl-pyrrolidinone. The reaction mixture was poured into 1N hydrochloric acid and extracted with ethyl acetate. The extract was washed with water twice and with brine once and thereafter dried over anhydrous sodium sulfate. The solvent was distilled off from the resulting extract in a vacuum, and the residue was purified by silica gel column chromatography, affording a compound II a (85 mg, 95%).

$^1$H-NMR (300 MHz, CDCl$_3$)δ: 3.60(s, 2H), 3.80(s, 3H), 5.10(s, 2H), 5.33(dd, J=5.0, 83. Hz, 1H), 5.48, 5.62(ABq, J=15.3 Hz, 2H), 5.87(d, J=5.0 Hz, 1H), 6.05(d, J=8.3 Hz, 1H), 6.85~7.85(m, 14H).

EXAMPLE 2

The same reaction procedure as in Example 1 was repeated with the exception of using 2 equivalents of aluminum foil. Consequently, the starting material disappeared almost completely 5 hours later to give a compound IIa (82 mg. 92%). The spectrum data of the resulting compound IIa was fully identical with that of the product of Example 1.

EXAMPLE 3

The same reaction procedure as in Example 1 was repeated with the exception of using 0.25 equivalent of aluminum chloride. Consequently, the starting material disappeared almost completely 3 hours later to give a compound IIa (82 mg. 92%). The spectrum data of the resulting compound IIa was fully identical with that of the product of Example 1.

EXAMPLE 4

The same reaction procedure as in Example 1 was repeated except that aluminum chloride was not used. Consequently, the starting material disappeared almost completely 5 hours later to give a compound IIa (83 mg. 93%). The spectrum data of the resulting compound IIa was fully identical with that of the product of Example 1.

EXAMPLE 5

The same reaction procedure as in Example 1 was repeated with the exception of using 0.25 equivalent of aluminum chloride and 3 equivalents of aluminum foil. Consequently, the starting material disappeared almost completely 5 hours later to give a compound IIa (80 mg. 89%). The spectrum data of the resulting compound IIa was fully identical with that of the product of Example 1.

EXAMPLE 6

The same reaction procedure as in Example 1 was repeated with the exception of using compound (Ib) ($R_1$=PhCH$_2$CONH, $R_2$=Ph, $R_3$=CHPh$_2$, X=Cl, Y=Cl, n=2). Consequently, compound IIb (83 mg. 92%) was obtained.

$^1$H-NMR (300 MHz, CDCl$_3$) δ: 3.61(s, 2H), 5.31(dd, J=4.4, 8.0 Hz, 1H), 5.57, 5.70(ABq, J=15.2 Hz, 2H), 5.84(d, J=4.4 Hz, 1H), 6.02(d, J=8.0 Hz, 1H), 6.81(s, 1H), 7.22~7.73(m, 20H).

EXAMPLE 7

The same reaction procedure as in Example 1 was repeated with the exception of using compound (Ic) ($R_1$=PhCH$_2$CONH, $R_2$=Ph, $R_3$=CH$_3$, X=Cl, Y=Cl, n=2). Consequently, compound IIc (89 mg. 94%) was obtained.

$^1$H-NMR (300 MHz, CDCl$_3$) δ: 3.59(s, 2H), 3.74(s, 3H), 5.33(dd, J=4.4, 8.0 Hz, 1H), 5.54, 5.64(ABq, J=15.0 Hz, 2H), 5.88(d, J=4.4 Hz, 1H), 6.02(d, J=8.0 Hz, 1H), 7.20~7.90(m, 10H).

EXAMPLE 8

The same reaction procedure as in Example 1 was repeated with the exception of using compound (Id) ($R_1$=PhCH$_2$CONH, $R_2$=Ph, $R_3$=CH$_2$C$_6$H$_4$OCH$_3$-p, X=Cl, Y=OSO$_2$CF$_3$, n=2). Consequently, compound IIa (68 mg. 90%) was obtained. The spectrum data of the resulting compound IIa was fully identical with that of the product of Example 1.

EXAMPLE 9

The same reaction procedure as in Example 1 was repeated with the exception of using compound (Ie) ($R_1$=PhCH$_2$CONH, $R_2$=Ph, $R_3$=CHPh$_2$, X=Cl, Y=OSO$_2$CF$_3$, n=2). Consequently, compound IIb (69 mg. 89%) was obtained. The spectrum data of the resulting compound IIb was fully identical with that of the product of Example 6.

EXAMPLE 10

The same reaction procedure as in Example 1 was repeated with the exception of using compound (If) ($R_1$=PhCH$_2$CONH, $R_2$=Ph, $R_3$=CH$_2$C$_6$H$_4$OCH$_3$-p, X=Cl, Y=OSO$_2$C$_6$H$_4$CH$_3$-p, n=2). Consequently, compound IIa (63 mg. 91%) was obtained. The spectrum data of the resulting compound IIa was fully identical with that of the product of Example 1.

EXAMPLE 11

The same reaction procedure as in Example 1 was repeated with the exception of using compound (Ig) ($R_1$=PhCH$_2$CONH, $R_2$=Ph, $R_3$=CHPh$_2$, X=Cl, Y=OSO$_2$C$_6$H$_4$CH$_3$-p, n=2). Consequently, compound IIb (67 mg. 90%) was obtained. The spectrum data of the resulting compound IIb was fully identical with that of the product of Example 6.

EXAMPLES 12 To 14

The same reaction procedure as in Example 1 was repeated with use of compound Ia and altering a zero-valent metal. Table 1 shows the results.

EXAMPLES 15 TO 20

The same reaction procedure as in Example 1 was repeated with use of compound Ia and altering Lewis acid. Table 2 shows the results.

EXAMPLES 21 TO 24

The same reaction procedure as in Example 1 was repeated with use of compound Ia and altering a solvent. Table 3 shows the results.

TABLE 1

| Example | zero-valent metal | yield (%) |
| --- | --- | --- |
| 12 | Mg | 88 |
| 13 | Zn | 92 |
| 14 | Sn | 85 |

TABLE 2

| Example | Lewis acid | yield (%) |
| --- | --- | --- |
| 15 | TiCl$_4$ | 82 |
| 16 | CaCl$_2$ | 92 |
| 17 | MgCl$_2$ | 89 |
| 18 | BiCl$_3$ | 87 |
| 19 | LiCl | 90 |
| 20 | BF$_3$.Et$_2$O | 89 |

TABLE 3

| Example | solvent | yield (%) |
| --- | --- | --- |
| 21 | dimethylformamide | 82 |
| 22 | dimethylacetamide | 85 |
| 23 | N-methyl-imidazolinone | 86 |
| 24 | tetrahydrofuran | 82 |

EXAMPLE 25

A 100 mg quantity of compound (Ia) ($R_1$=PhCH$_2$CONH, $R_2$=Ph, $R_3$=CH$_2$C$_6$H$_4$OCH$_3$-p, X=Cl, Y=Cl, n=2), 0.5 equivalent of aluminum chloride and 10 equivalents of aluminum foil were measured out into a 10-ml flask of the egg plant type, followed by stirring at room temperature for 5 hours with addition of 2 ml of N-methyl-pyrrolidinone. The reaction mixture was poured into ice-water and extracted with ethyl acetate. The extract was washed with water twice and with saturated saline once and thereafter dried over anhydrous sodium sulfate. The solvent was distilled off from the resulting extract in a vacuum, and the residue was purified by silica gel column chromatography, affording a compound m a (66 mg, 90%).

$^1$H-NMR (CDCl$_3$) δ: 3.42(d, J=17.8 Hz, 1H), 3.72(d, J=17.8 Hz, 1H), 3.58(d, J=16.4 Hz, 1H), 3.64(d, J=16.4 Hz, 1H), 3.79(s, 3H), 4.96(d, J=5.1 Hz, 1H), 5.21(s, 2H), 5.79 (dd, J=5.1, 9.2 Hz, 1H), 6.39(d, J=9.2 Hz, 1H), 6.82~7.40(m, 9H).

EXAMPLE 26

The same reaction procedure as in Example 1 was repeated with the exception of using compound (Ib) ($R_1$=

PhCH$_2$CONH, R$_2$=Ph, R$_3$=CHPh$_2$, X=Cl, Y=Cl, n=2). Consequently, compound IIIb (66 mg. 88%) was obtained.

$^1$H-NMR (CDCl$_3$) δ: 3.43(d, J=18.9 Hz, 1H), 3.58(d, J=16.2 Hz, 1H), 3.65(d, J=16.2 Hz, 1H), 3.73(d, J=18.9 Hz, 1H), 4.99(d, J=4.8 Hz, 1H), 5.83(dd, J=4.8, 9.3 Hz, 1H), 6.24(d, J=9.3 Hz, 1H), 6.97(s, 1H), 7.21~7.42(m, 15H).

EXAMPLE 27

The same reaction procedure as in Example 1 was repeated with the exception of using compound (Id) (R$_1$=PhCH$_2$CONH, R$_2$=Ph, R$_3$=CH$_2$C$_6$H$_4$OCH$_3$-p, X=Cl, Y=OSO$_2$CF$_3$, n=2). Consequently, compound III a (55 mg. 89%) was obtained. The spectrum data of the resulting compound III a was fully identical with that of the product of Example 25.

EXAMPLE 28

The same reaction procedure as in Example 25 was repeated with the exception of using compound (Ie) (R$_1$=PhCH$_2$CONH, R$_2$=Ph, R$_3$=CHPh$_2$, X=Cl, Y=OSO$_2$CF$_3$, n=2). Consequently, compound III b (57 mg. 89%) was obtained. The spectrum data of the resulting compound III b was fully identical with that of the product of Example 26.

EXAMPLE 29

The same reaction procedure as in Example 25 was repeated with the exception of using compound (If) (R$_1$=PhCH$_2$CONH, R$_2$=Ph, R$_3$=CH$_2$C$_6$H$_4$OCH$_3$-p, X=Cl, Y=OSO$_2$C$_6$H$_4$CH$_3$-p, n=2). Consequently, compound III a (51 mg. 85%) was obtained. The spectrum data of the resulting compound III a was fully identical with that of the product of Example 25.

EXAMPLE 30

The same reaction procedure as in Example 25 was repeated with the exception of using compound (Ig) (R$_1$=PhCH$_2$CONH, R$_2$=Ph, R$_3$=CHPh$_2$, X=Cl, Y=OSO$_2$C$_6$H$_4$CH$_3$-p, n=2). Consequently, compound III b (50 mg. 80%) was obtained. The spectrum data of the resulting compound III b was fully identical with that of the product of Example 26.

EXAMPLES 31 TO 33

The same reaction procedure as in Example 25 was repeated with use of compound Ia and altering a zero-valent metal. Table 4 shows the results.

EXAMPLES 34 TO 37

The same reaction procedure as in Example 25 was repeated with use of compound Ia and altering Lewis acid. Table 5 shows the results.

EXAMPLES 38 TO 40

The same reaction procedure as in Example 25 was repeated with use of compound Ia and altering a solvent. Table 6 shows the results.

TABLE 4

| Example | zero-valent metal | yield (%) |
|---|---|---|
| 31 | Mg | 80 |
| 32 | Zn | 85 |
| 33 | Sn | 82 |

TABLE 5

| Example | Lewis acid | yield (%) |
|---|---|---|
| 34 | TiCl$_4$ | 80 |
| 35 | CaCl$_2$ | 87 |
| 36 | MgCl$_2$ | 85 |
| 37 | BiCl$_3$ | 79 |

TABLE 6

| Example | solvent | yield (%) |
|---|---|---|
| 38 | dimethylformamide | 85 |
| 39 | dimethylacetamide | 87 |
| 40 | N-methyl-imidazolidinone | 87 |

REFERENCE EXAMPLE 1

The following shows a synthetic route of cefaclor from β-lactam compound of the invention.

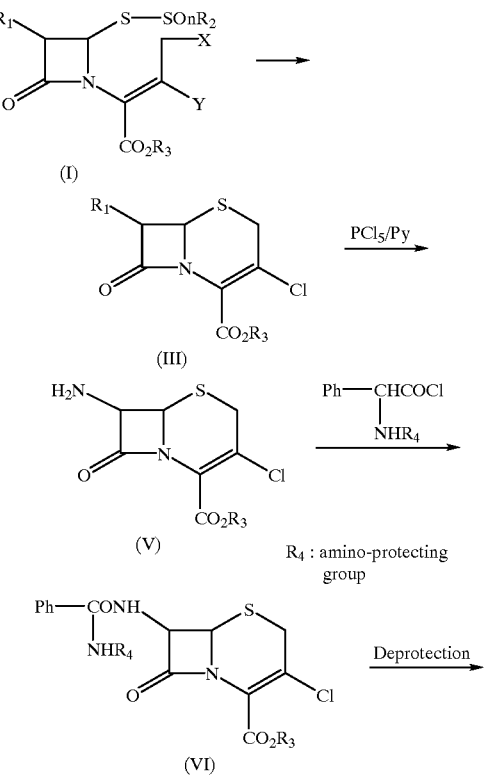

-continued

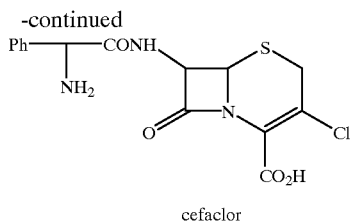

cefaclor

INDUSTRIAL APPLICABILITY

According to the present invention, a β-lactam halide compound represented by the formula (I) serving as the starting material can be converted into an allenyl β-lactam compound represented by the formula (II) and a 3-halocephem compound of the formula (III) merely by altering the reaction conditions, each in a simple procedure stably in a high yield and with a high purity.

We claim:

1. A process for preparing an allenyl β-lactam compound represented by formula (II) comprising contacting a β-lactam halide compound represented by formula (I) with a zero-valent metal selected from the group consisting of aluminum, magnesium, zinc, iron, nickel, tin and lead, for a time sufficient for said β-lactam halide compound to be reduced to said allenyl β-lactam compound; wherein said formula (I) is:

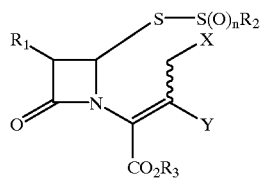

(I)

wherein $R_1$ is a hydrogen atom, amino or protected amino, $R_2$ is benzothiazol, thiazol, triazol, tetrazol, phenyl which is unsubstituted or substituted with up to 5 substituents, or naphthyl which is unsubstituted or substituted with up to 7 substituents, said substituents being independently selected from nitro, cyano, phenl, halogen atoms, straight-chain or branched $C_{1-4}$ alkoxyl groups, straight-chain or branched $C_{1-4}$ alkylthio groups, straight-chain or branched $C_{1-4}$ alkylsulfonyloxy groups, aromatic sulfonyloxy, straight-chain or branched $C_{1-4}$ alkyl groups, amino, amino which has as a substituent one or two straight-chain or branched $C_{1-4}$ alkyl groups, hydroxyl, acyloxy group represented by R'COO— wherein R' is phenyl, tolyl, or straight-chain or branched $C_{1-4}$ alkyl group, acyl group represented by R'CO—wherein R' is as defined above, n is 0 to 2, $R_3$ is a hydrogen atom or carboxylic acid protective group, X is a halogen atom, and Y is a leaving group; and said formula (II) is:

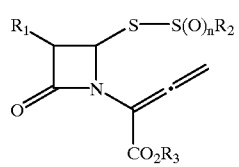

(II)

wherein $R_1$, $R_2$, n and $R_3$ are as defined above.

2. A process for preparing a 3-halocephem compound represented by formula (III) comprising contacting a β-lactam halide compound represented by the formula (I) with a zero-valent metal selected from the group consisting of aluminum, magnesium, zinc, iron, nickel, tin and lead, for a time sufficient for said β-lactam halide compound to be reduced to an allenyl β-lactam compound of formula (II) and for ring closure of said allenyl β-lactam compound to occur to form said 3-halocephem compound; wherein said formula (I) is:

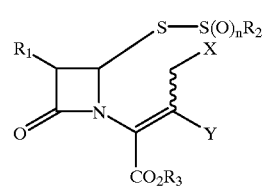

(I)

wherein $R_1$ is a hydrogen atom, amino or protected amino, $R_2$ is benzothiazol, thiazol, triazol, tetrazol, phenyl which is unsubstituted or substituted with up to 5 substituents, or naphthyl which is unsubstituted or substituted with up to 7 substituents, said substituents being independently selected from nitro, cyano, phenyl, halogen atoms, straight-chain or branched $C_{1-4}$ alkoxyl groups, straight-chain or branched $C_{1-4}$ alkylthio groups, straight-chain or branched $C_{1-4}$ alkylsulfonyloxy groups, aromatic sulfonyloxy, straight-chain or branched $C_{1-4}$ alkyl groups, amino, amino which has as a substituent one or two straight-chain or branched $C_{1-4}$ alkyl groups, hydroxyl, acyloxy group represented by R'COO— wherein R' is phenyl, tolyl, or straight-chain or branched $C_{1-4}$ alkyl group, acyl group represented by R'CO—wherein R' is as defined above, n is 0 to 2, $R_3$ is a hydrogen atom or carboxylic acid protective group, X is a halogen atom, and Y is a leaving group; said formula (II) is:

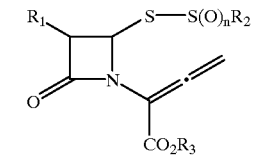

(II)

wherein $R_1$, $R_2$, n and $R_3$ are as defined above; and said formula (III) is:

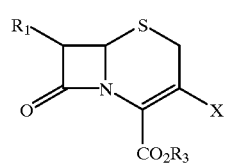

(III)

wherein $R_1$, $R_3$ and X are as defined above.

3. A process as defined in claim 1 wherein the zero-valent metal is used in an amount of 1 to 50 moles per mole of the compound of the formula (I).

4. A process as defined in claim 1 wherein the reaction is conducted in the presence of a Lewis acid.

5. A process as defined in claim 2 wherein the zero-valent metal is used in an amount of 1 to 50 moles per mole of the compound of the formula (I).

6. A process as defined in claims 2 wherein the reaction is conducted in the presence of a Lewis acid.

* * * * *

UNITED STATES PATENT AND TRADEMARK OFFICE
CERTIFICATE OF CORRECTION

PATENT NO. : 5,986,091
DATED : Nov. 16, 1999
INVENTOR(S) : Sigeru TORII et al.

It is certified that error appears in the above-indentified patent and that said Letters Patent is hereby corrected as shown below:

On the first page, left column, item [22] (PCT filed), delete "Mar. 7, 1996" and insert therefor --Mar. 7, 1997--.

Signed and Sealed this

Ninth Day of May, 2000

Attest:

Attesting Officer

Q. TODD DICKINSON

Director of Patents and Trademarks